United States Patent [19]
Yun et al.

[11] Patent Number: 5,545,300
[45] Date of Patent: Aug. 13, 1996

[54] LOW POWER CONSUMPTION TYPE THIN FILM GAS SENSOR

[75] Inventors: Dong H. Yun, Kyungki-do; Kyu C. Lee, Seoul; Hyung K. Hong, Kyungki-do; Hyeon S. Park; Chul H. Kwon, both of Seoul; Hyun W. Shin, Kyungki-do, all of Rep. of Korea

[73] Assignee: Goldstar Co., Ltd., Seoul, Rep. of Korea

[21] Appl. No.: 297,606

[22] Filed: Aug. 29, 1994

[30] Foreign Application Priority Data

Dec. 4, 1993 [KR] Rep. of Korea ............... 1993-26474

[51] Int. Cl.⁶ .................... G01N 27/12; G01N 27/407
[52] U.S. Cl. .................. 204/424; 204/426; 204/431; 422/98
[58] Field of Search .................. 204/421, 424–429, 204/431; 422/98

[56] References Cited

U.S. PATENT DOCUMENTS

| | | | |
|---|---|---|---|
| 4,706,493 | 11/1987 | Chang et al. | 422/98 |
| 4,953,387 | 9/1990 | Johnson et al. | 422/98 |
| 5,211,053 | 5/1993 | Nolting et al. | 422/98 |
| 5,228,975 | 7/1993 | Yamada et al. | 204/424 |
| 5,262,127 | 11/1993 | Wise et al. | 422/98 |

*Primary Examiner*—T. Tung
*Attorney, Agent, or Firm*—John P. White

[57] ABSTRACT

This invention relates to a low power consumption type thin film gas sensor and method for fabricating the same. The gas sensor includes a silicon substrate having a window in the central part of one side thereof, masking material formed on the one side thereof except the window, a supporting film formed of an etch stop layer and a glass film on the other side of the substrate, heaters and temperature sensors arranged in parallel on the supporting film facing the window, an interlayer insulation film formed on the supporting film to cover the heaters and the temperature sensors, sensing film electrodes formed on the interlayer insulation film, and a sensing film formed on the interlayer insulation film so as to cover the sensing film electrodes for sensing a particular gas.

17 Claims, 5 Drawing Sheets

LOW POWER CONSUMPTION TYPE THIN FILM GAS SENSOR

FIELD OF THE INVENTION

This invention relates to a low power consumption type thin film gas sensor and fabrication method thereof, more particularly to a thin film gas sensor and fabrication method thereof which can minimize the power consumption for heating heaters thereof which heat to a specific high temperature a sensing film thereof to enhance the sensitivity of the sensing film to a particular gas by forming a supporting film of a heat generation part with a material and structure having low heat loss.

BACKGROUND OF THE INVENTION

A gas sensor is a sensor for sensing presence of a particular gas, there are, depending on the gas to be sensed by the sensing film of a sensor, a sensor for sensing CO, a sensor for sensing $(CH_3)^{3N}$ gas generated when fish in a refrigerator goes bad, a sensor for sensing $CH_3SH$ gas generated when vegetables go bad and a sensor for sensing $C_2H_5OH$, etc. In general, what we should take into account as basic requisite a gas sensor has to have is to be compact and low power consumptive, in addition to high sensitivity, excellent selectivity and high speed of response.

Such a gas sensor contains a heater in the element to enhance the sensitivity of a sensing film to sense a particular gas by heating the sensing film to a specific temperature (normally to 200 to 500 deg. C.), while maintaining the lowest possible power consumption.

In order to make the power consumption lower, the material of the heater itself should be highly efficient as a heat generating material, and loss of the heat generated in the heater to outsise should be minimized.

When a heater is to be heated to a specific temperature difference $\Delta T$, in general, the amount of heat loss P to outside is expressed as follows;

$$P = P_m + P_R + P_A,$$

where, $P_m$ is heat loss through the supporting film of the sensor, $P_R$ is heat loss due to the radiation, and $P_A$ is heat loss through circumferential air.

wherein, since the $P_R$ is relatively very small value, and the $P_A$ is small value caused by the geometry of the heating part, it is possible to reduce the heat loss P just by reducing the $P_m$.

The heat loss through the supporting film Pm of a sensor can be expressed as follows;

$$P_m = \frac{K \cdot \sigma \cdot h \cdot \Delta T}{\ln(u/a)}$$

where, K is a constant,

σ is heat conductivity of the supporting film, h is thickness of the supporting film, u is width of the supporting film, and a is length of the heat generation part.

As can be seen from the equation, to reduce heat loss through the supporting film, either the supporting film should be of low heat conductive material with reduced thickness, or the ratio of the length of the heating part to the width of the supporting film should be adjusted.

A conventional thin film gas sensor fabricated considering the foregoing condition could have reduced the heat loss of a heater by providing, after forming a supporting film, a heater, and a sensing film on one side of a silicon wafer, a window formed by carrying out an anisotropic etching of the other side of the wafer.

A supporting film of a thin film gas sensor exerts a very important influence on the characteristics such as efficiency, reliability, etc. of the sensor, depending on the structure, and the thermal, electrical and mechanical properties of the supporting film.

The supporting film is formed by a silicon wafer having a supporting film formed on one side thereof which is etched from the back thereof in an etching solution until an appropriate thickness thereof is left when the etching is stopped.

Such an etch stop is caused by an exposure of, in most cases, boron doped $P^+$ type silicon layer, a silicon oxide ($SiO_2$) film, or a silicon nitride ($Si_3N_4$) film.

Therefore, in order to form a supporting film of predetermined thickness, though it is necessary to carry out an anisotropic etching of a silicon wafer having the film formed thereon to an exact thickness, it is difficult to control forming the exact thickness of the supporting film due the occurance of small amount of etching of the boron doped silicon layer (hereinafter called "$P^+$–Si") or the silicon oxide film in an anisotropic etching solution (KOH water solution).

However, since the silicon nitride ($Si_3N_4$) film is not susceptible to an etching solution at all, if underlayer of the supporting film is formed of the silicon nitride ($Si_3N_4$) film, an exact thickness of the supporting film can be obtained.

FIG. 1 is a section of a conventional thin film gas sensor.

Referring to FIG. 1, a thin film gas sensor includes a supporting film 2 having a silicon oxide film 2a, a silicon nitride film 2b and a silicon oxide film 2c deposited stacked on a silicon substrate 1 to a thickness of 2.5 μm, 0.2 μm, 2.5 μm, respectively, and having a NiFe metal alloy deposited on the supporting film 2, which is subjected to a patterning to form heaters 3 and temperature sensors 4.

In this instant, size of the active area a of the heaters 3 is made to be 450 μm×450 μm.

After forming the heaters 3 and the temperature sensors 4 on the supporting film 2 as described above, a passivation layer 5 is formed thereon using $SiON_x$.

After forming gas sensing elements 8 each having a sensing electrode 6 and a sensing film 7 on the passivation layer 5, the back of the silicon substrate 1 is subjected to an anisotropic etching in KOH water solution.

This completes fabrication of a conventional thin film gas sensor 10 having a supporting film 2 formed of deposited, stacked structure of $SiO_2$, $Si3N_4$ and $SiO_2$ thereon.

The characteristics of the heater of a conventional thin film gas sensor is shown in FIG. 2.

It can be shown that a conventional thin film gas sensor consumes 70 mw to heat the heat generation part of the heater thereof to 300 deg. C., about 340 mw/mm² of the heat generation part, and resistence of the temperature sensor is about 700 Ω at 300 deg. C.

The thin film gas sensor fabricated according to the foregoing process using, for the supporting film, single layered film of $P^+$–Si, $SiO_2$ or $Si_3N_4$, or multiple layered film of $SiO_2/Si_3N_4/SiO_2$ has problems of having a difficulty in forming a supporting film having an exact predetermined thickness due to small amount of etch of $P^+$–Si or $SiO_2$, $SiO_2/Si_3N_4/SiO_2$ in KOH water solution during the anisotropic etching, and having a limit in reducing the power consumption of the heater due to $P^+$–Si and $Si_3N_4$ having relatively high heat conduction, which leads to a greater heat loss.

SUMMARY OF THE INVENTION

Accordingly, the object of this invention for solving the foregoing problems is to provide a low power consumption type thin film gas sensor which can minimize the power consumption of the heater for heating to a specific high temperature the gas sensing film to enhance the sensitivity of the gas sensing film to a particular gas by forming the supporting film of the heat generation part of the gas sensor with glass having small heat loss.

Another object of this invention is to provide a method for fabricating a low power consumption type thin film gas sensor which can minimize the power consumption of the heater thereof and can control the thickness of the supporting film exactly by using glass films and silicon nitride films having low heat conductivities for the supporting film.

These and other objects and features of this invention can be achieved by providing a low power consumption type thin film gas sensor including a silicon substrate having a window in the central part of one side thereof, masking material formed on the one side thereof except the window, a supporting film formed of an etch stop layer and a glass film on the other side of the substrate, heaters and temperature sensors arranged in parallel on the supporting film facing the window, an interlayer insulation film formed on the supporting film to cover the heaters and the temperature sensors, sensing film electrodes formed on the interlayer insulation film, and a sensing film formed on the interlayer insulation film so as to cover the sensing film electrodes for sensing a particular gas.

And, the method for fabricating a low power consumption type thin film gas sensor includes processes for depositing a silicon nitride film on one side of a silicon substrate, forming a supporting film by depositing a silicon nitride film and a glass film successively on the other side of the substrate, forming heaters and temperature sensors arranged in parallel on the supporting film, forming an interlayer insulation film on the supporting film the heaters and the temperature sensors are formed thereon, forming sensing film electrodes on the interlayer insulation film, forming a sensing film on the interlayer insulation film to cover the sensing film electrodes, forming etching window exposing the silicon substrate by carrying out etching of the parts corresponding to the temperature sensors and the heaters of the nitride film formed on the one side of the silicon substrate after completion of the sensing film forming process, and forming a window by carrying out an anisotropic etching of the exposed silicon substrate using the masking material as a mask.

DETAILED DESCRIPTION OF THE PREFERRED EMBODIMENT

FIGS. 3(a) to 3(e) show processes for fabricating a thin film gas sensor in accordance with this invention.

The process for fabricating a thin film gas sensor in accordance with this invention is as follows.

Figure 1:
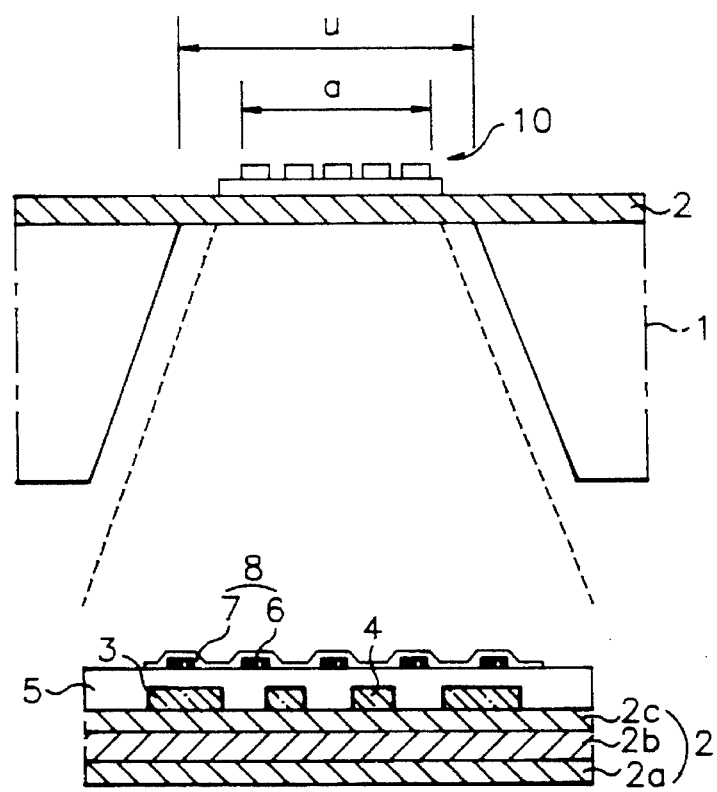
FIG. 1 is a section of a conventional thin film gas sensor.
Figure 2:
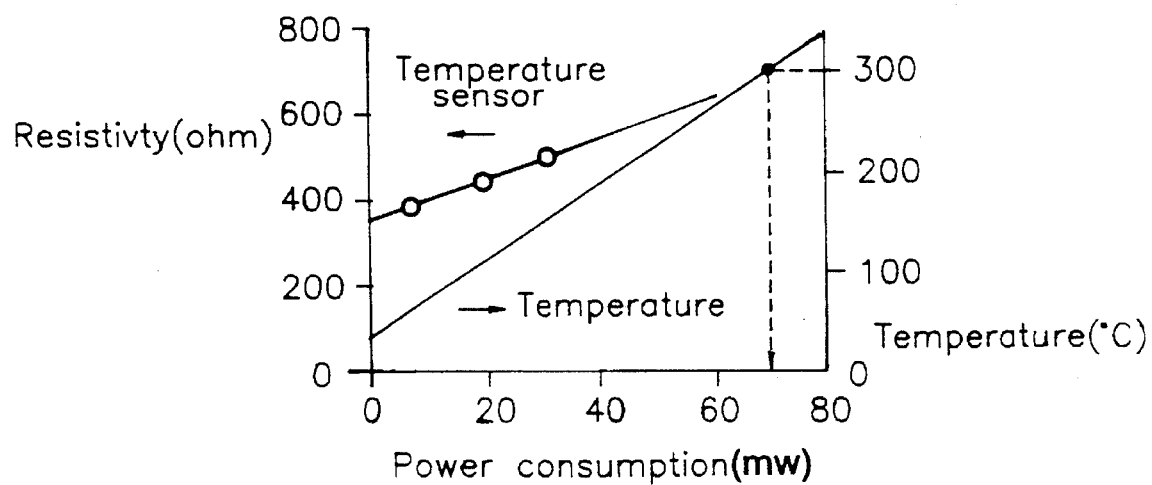
FIG. 2 is a power consumption characteristic curve of a heater of the thin film gas sensor shown in FIG. 1.
Figure 3A:
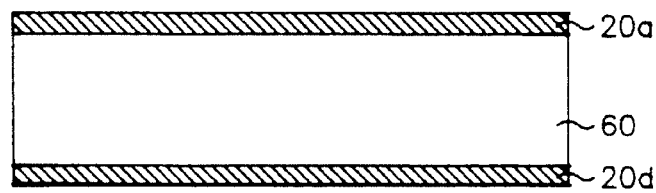
FIGS. 3(a) to 3(e) show processes for fabricating a thin film gas sensor in accordance with this invention.

First, as shown in FIG. 3(a), silicon nitride ($Si_3N_4$) films 20a and 20d are deposited on both sides of a silicon substrate 60 each to a thickness of 500 Angstroms to 2500 Angstroms with low pressure chemical vapor deposition (LPCVD) method, wherein the silicon nitride film 20d deposited at the back of the silicon substrate 60 serves as a mask at the time of carrying out anisotropic etching of the silicon substrate 60 in following process and the silicon nitride film 20a at the front thereof serves as an etch stop layer.

Figure 3B:
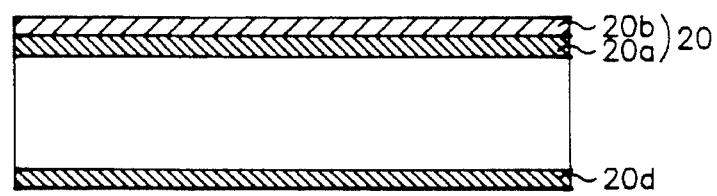

Then, a glass film 20b is deposited with atmospheric pressure chemical vapor deposition (APCVD) method to a thickness of 5000 Angstroms to 3 um on the silicon nitride film deposited on the silicon substrate 60. A supporting film 20 having a nitride film 20a and a glass film 20b as shown in FIG. 3(b), wherein the glass film 20b, being one of PSG (phosphosilicate glass), BSG (borosilicate glass) or BPSG (borophosphosilicate glass), serves as a supporting film having low heat conductivity.

Figure 3C:
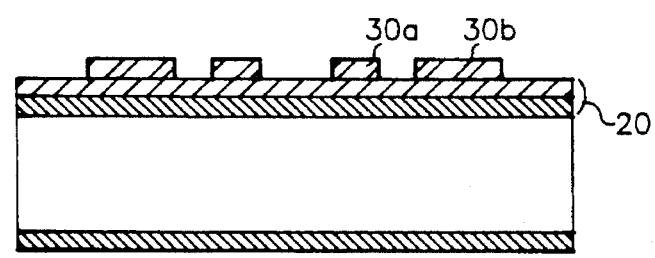

Next, as shown in FIG. 3(c), heaters 30b and temperature sensors 30a are formed in parallel on the supporting film 20 formed in the foregoing process so that each of the areas of the heat generation parts of the gas sensor is to be 0.588 mm×0.588 mm.

The heater 30b and the temperature sensor 30a are deposited to a thickness of about 5000 Angstroms to 3 um using metals such as Pt/Ta. In this instant, the length of the heat generation part is formed to be less than ½ of the width of the supporting film.

The tantalum (Ta) used for the heat generation part at forming the heaters 30b and the temperature sensors 30a is deposited under a platinum (Pt) layer as a means for enhancing the adhesive force between the platinum layer and the glass film, preferably to a thicknes of 200 Angstroms to 700 Angstroms. And the platinum, being a high temperature material, can be used for the heaters as well as for the temperature sensors due to its heat generation chatacteristics and exhibits excellent agreement with resistance law based on the change of temperature.

After forming the heaters and the temperature sensors in the foregoing process, an interlayer insulation film 40 is formed by depositing an silicon nitride film with sputtering method.

In this invention, a silicon nitride film having an excellent insulation property and a high heat conductivity is used as the interlayer insulation film 40 for easy transfer of the heat generated in the heater 30b to a sensing film to be formed in a process to be described later.

Sensing film electrodes 50a are formed by depositing metals such as Pt/Ta to a thickness of about 4000 Angstroms to 6000 Angstroms and patterning it, and a sensing film 50 is formed so as to cover the sensing film electrodes 50a.

Figure 3D:
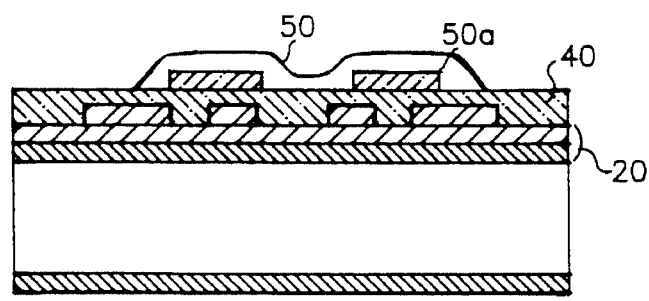

Through the foregoing process, a sensing element having sensing film electrodes 50a and a sensing film 50 as shown in FIG. 3(d).

Herein, the sensing film 50 is of SnO2 doped with 1 wt % of palladium, preferably to a thinkness of 1000 Angstroms to 5000 Angstroms.

After completion of the foregoing processes for the front surface of the silicon substrate 60, the silicon nitride film 20d formed at the back of the silicon substrate 60 is etched with reactive ion etching (RIE) method to form an etching window.

Figure 3E:
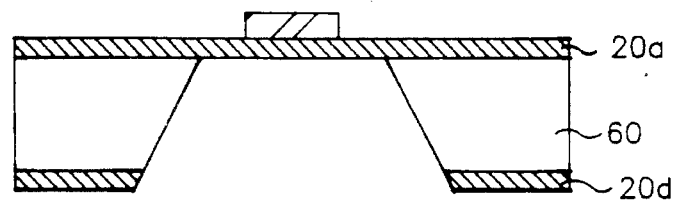

Then the exposed silicon substrate 60 is subjected to an anisotropic etching in KOH solution using the silicon nitride film 20d at the back thereof as a mask. The progress of etch stops at the silicon nitride film 20a to obtain a thin film gas sensor as shown in FIG. 3(e).

Figure 4:
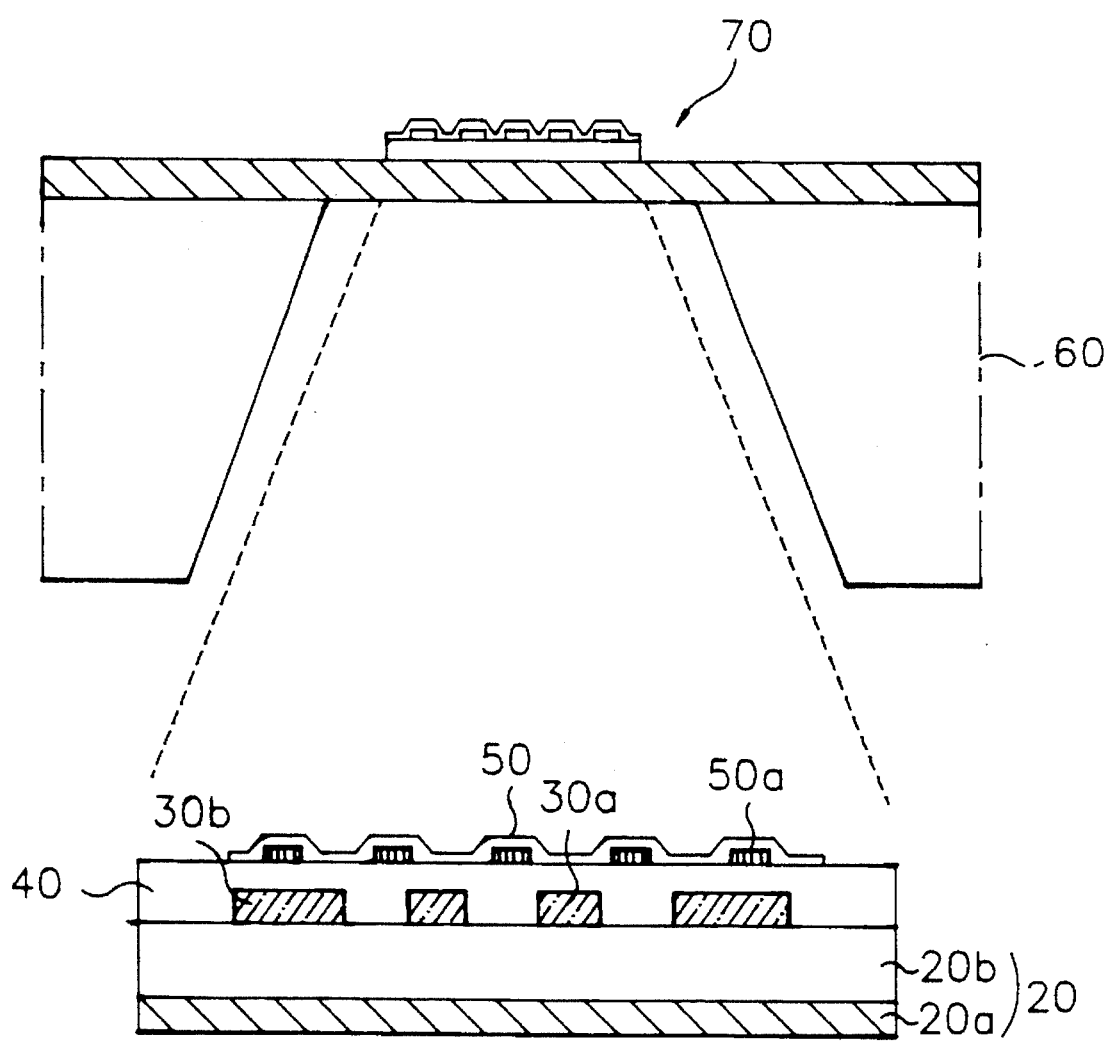
FIG. 4 is a section of the thin film gas sensor fabricated in accordance with the processes of FIGS. 3(a) to 3(e).

FIG. 4 is a section of of a thin film gas sensor of low power consumption type in accordance with this invention fabricated through the processes of FIGS. 3(a) to 3(e).

As shown in FIG. 4, a thin film gas sensor 70 of low power consumption type in accordance with this invention includes a supporting film 20, having a silicon nitride film 20a and a glass film 20b, serving as an etch stop layer formed on one side of the silicon substrate 60, heaters 30b and temperature sensors 30a formed on the supporting film 20 arranged in parallel, an interlayer insulation film 40 formed on the supporting film 20 so as to cover the heaters 30b and the temperature sensors 30a, a sensing element having sensing film electrodes 50a and a sensing film 50 formed on the interlayer insulation film 40, a window formed on the other side of the silicon substrate 60, and a silicon nitride film 20d formed on the other side thereof with no window having been formed thereon.

The gas sensor in accordance with this invention enables control of the thickness of the supporting film precisely since the supporting film 20 having the silicon nitride film 20a and the glass film 20b can not be etched due to the silicon nitride film 20a serving as an etch stop layer while carrying out an anisotropic etching of the silicon substrate 60 in the following process, and can sense a particular gas well since the sensing film 50 can be heated to a specific temperature due to the glass film 20b having a low heat conductivity that prevents loss of heat through the supporting film 20 at the time of heating the sensing film 50 to a high temperature.

Moreover, the thickness of the supporting film 20 can be reduced because a conventional supporting film 20 uses three layers, a silicon oxide film 2a, a silicon nitride film 2b and a silicon oxide film 2c, whereas the supporting film of this invention uses two layers, a silicon nitride film 20a and a glass film 20b.

As for the heaters 30b and the temperature sensors 30a, multiple metal layers are used.

Platinum, being a high temperature material, has an excellent heat generation characteristic and exhibits an excellent agreement with the resistance law based on temperature, and tantalum is used to enhance the adhesive force between the platinum and the glass film.

The heater 30b is provided for heating the sensing film 50 to a specific temperature to enhance the sensitivity of the sensing film 50 for a particular gas, and the temperature sensor 30a is provided to sense the temperature of the heater 30a.

A nitride film is used as an interlayer insulation film 40, which silicon nitride film helps the sensing film 50 be heated to a specific temperature to sense a particular gas well because the silicon nitride film having an excellent insulation property and a high heat conductivity permits good transfer of the heat generated in the heater 30b to the sensing film.

As for the sensing film electrode 50a, multiple layers of metal films such as Pt/Ta are used, and as for the sensing film 50, $SnO_2$ doped with 1 wt % of palladium is used.

The sensing film electrode 50a is provided for measuring the resistance component of the sensing film 50, and the sensing film 50 is provided for sensing a particular gas.

The nitride film 20d formed at the back of the silicon substrate 60 serves as a masking material while carrying out an anisotropic etching of the silicon substrate 60.

The characteristics of the thin film gas sensor fabricated through the foregoing processes obtained through tests are shown in FIGS. 5 to 8.

Figure 5:
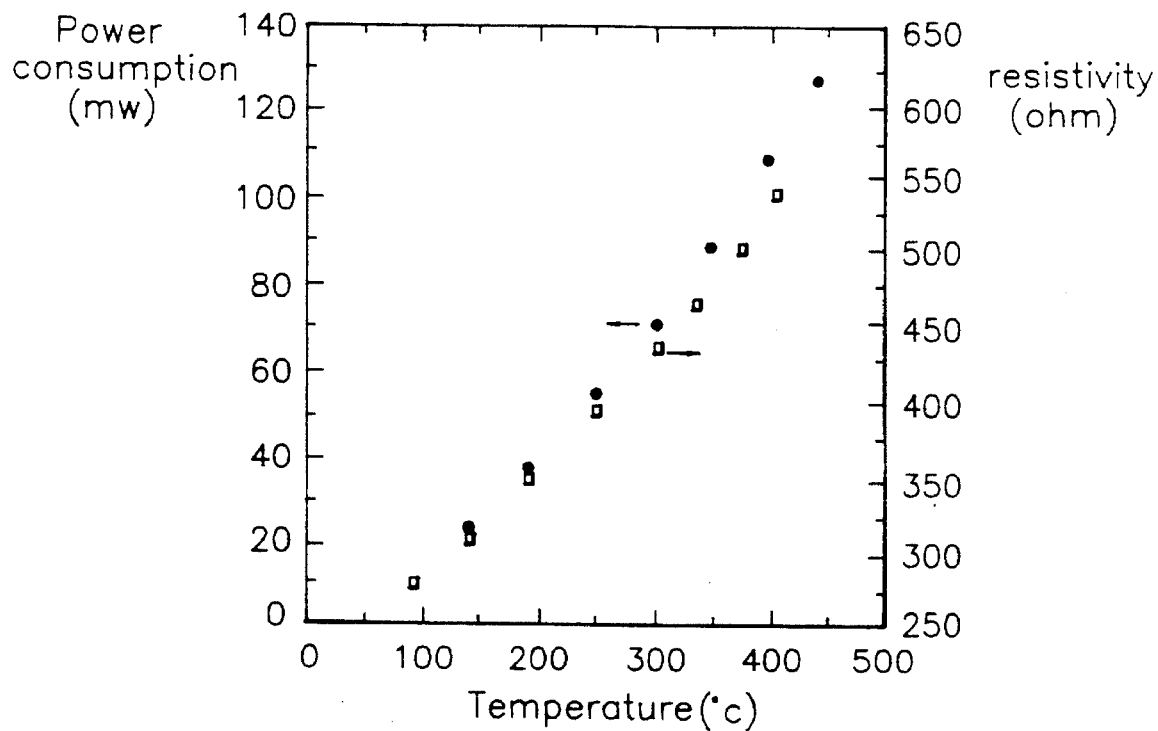
FIG. 5 is a graph showing both power consumption of a heater required for heating a sensing film and resistance of sensors based on temperature for a thin film gas sensor in accordance with this invention.

FIG. 5 is a graph showing both the power consumption of a heater required to heat a sensing film and the resistance of sensors at the heated temperature.

Referring to FIG. 5, it can be known that, with this invention, the power consumption of the heaters for heating the sensing film 50 to 300 deg. C., is 70 mW, 202 mW/mm$^2$ for the heat generation part having an area of 0.588×0.588 mm$^2$, is much lower than the power consumption, being 340 mW/mm$^2$ for the heat generation part of a conventional sensor.

In conclusion, by controlling the properties of the supporting film 20 such as the heat conductivity ($\sigma$), the thickness (h) and the ratio of the length to the heat generation part (u/a), it is possible to reduce the power consumption of the heater.

Figure 6:
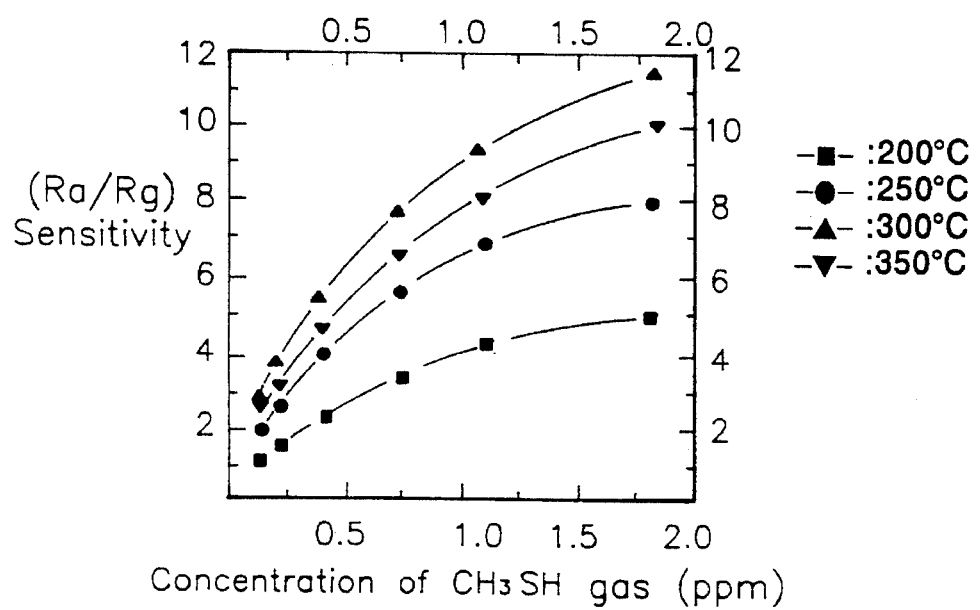
FIG. 6 is a graph showing change of sensivity of CH3SH gas based on the change of temperature for a thin film gas sensor in accordance with this invention.

Characteristics shown as graph in FIG. 6 could have been obtained as the result of measurements of the sensitivity based on the density of $CH_3SH$ gas while changing the temperature of the sensing film 50 with the heater 30b formed in the sensing element.

Referring to FIG. 6, the sensitivity of the sensing film 50 to a gas can be expressed as Ra (resistance of the sensing film in air)/Rg (resistance of the sensing film at exposure to a gas), it can be known that the sensor according to this invention can exihibit a sufficient sensitivity to $CH_3SH$ gas when heated to a temperature over 250 deg. C.

Figure 7:
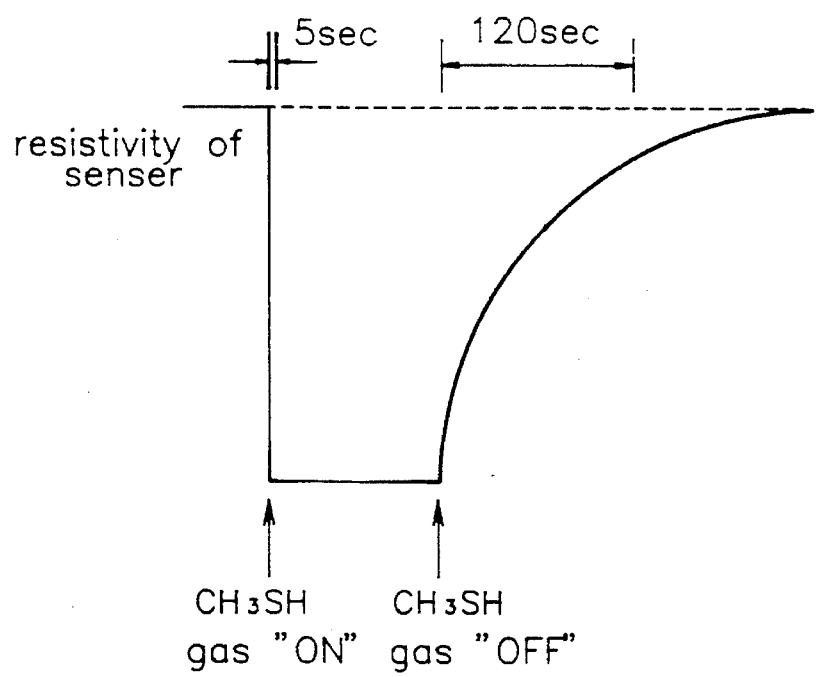
FIG. 7 shows the response characteristic of the sensor of this invention to CH3SH gas.

Shown in FIG. 7 is a response characteristic of a sensor to $CH_3SH$ gas, wherein it can be shown that the speed of response is about 5 seconds and the recovery characteristic is excellent when the sensor is exposed to $CH_3SH$ gas in a density of 0.2 ppm at 250 deg. C.

Figure 8:
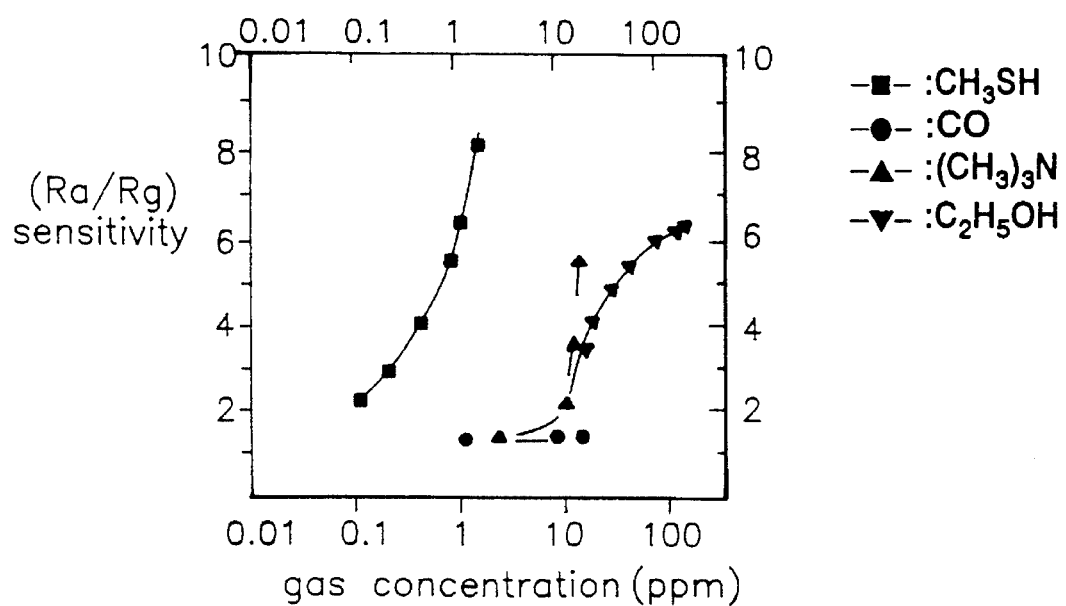
FIG. 8 is a graph showing the selectivity of the sensor of this invention to various gases.

Shown in FIG. 8 is result of tests for checking the sensitivity of the sensing film 50 of the thin film gas sensor in accordance with this invention to various gases.

Referring to FIG. 8, it can be seen that sensitivities to CO, $(CH_3)_3N$ and $C_2H_5OH$ are relatively lower than the sensitivity to $CH_3SH$.

By this, it can be known that the sensor in accordance with this invention has an excellent selectivity to $CH_3SH$ gas.

As has been explained, a thin film gas sensor in accordance with this invention has the advantages of reducing the power consumption of the heater and the capability of forming the thin supporting film precisely as the result of forming the supporting film using glass having a heat conductivity lower than the materials at use presently, and forming an etch stop film using a silicon nitride film.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirits and scope of the appended claims.

What is claimed is:

1. A low power consumption type thin film gas sensor comprising:

a silicon substrate having a window in the central part of one side thereof:

masking material formed on the one side thereof except the window;

a supporting film formed of an etch stop layer and a glass film on the other side of the substrate;

heaters and temperature sensors arranged in parallel on the supporting film facing the window, said heaters and temperature sensors having a fixed length of heat generation part;

an interlayer insulation film formed on the supporting film to cover the heaters and the temperature sensors, sensing film electrodes formed on the interlayer insulation film; and, a sensing film formed on the interlayer insulation film so as to cover the sensing film electrodes for sensing a particular gas.

2. The thin film gas sensor as claimed in claim 1, wherein a silicon nitride film is used for the masking material.

3. The thin film gas sensor as claimed in claim 2, wherein the thickness of the silicon nitride film is 500 Angstroms to 2500 Angstroms.

4. The thin film gas sensor as claimed in claim 1, wherein a silicon nitride film is used for the etch stop layer of the supporting film.

5. The thin film gas sensor as claimed in claim 4, wherein the thickness of the silicon nitride film is 500 Angstroms to 2500 Angstroms.

6. The thin film gas sensor as claimed in claim 1, wherein one of PSG (phosphosilicate glass), BSG (borosilicate glass) or BPSG (borophosphosilicate glass) film is used for the glass film.

7. The thin film gas sensor as claimed in claim 6, wherein the thickness of the glass film is 5000 Angrtroms to 3 um.

8. The thin film gas sensor as claimed in claim 1, wherein the heaters and the temperature sensors are formed of multiple metal layers.

9. The thin film gas sensor as claimed in claim 8, wherein the heaters and the temperature sensors are formed of multiple metal layers of Pt/Ta.

10. The thin film gas sensor as claimed in claim 9, wherein the thickness of the heaters and temperature sensors are 5000 Angstroms to 3 μm.

11. The thin film gas sensor as claimed in claim 9, wherein the tantalum layer serves for enhancing the adhesive force between the platinum layer and the glass film of the supporting film.

12. The thin film gas sensor as claimed in claim 11, wherein the thickness of the tantalum layer is 200–700 Angstroms.

13. The thin film gas sensor as claimed in claim 1, wherein the length of the heat generation part of the heaters and the temperature sensors is less than ½ of the width of the supporting film.

14. The thin film gas sensor as claimed in claim 1, wherein a silicon nitride film is used for the interlayer insulation film.

15. The thin film gas sensor as claimed in claim 1, wherein multiple metal layers of Pt/Ta are used for the sensing film electrodes.

16. The thin film gas sensor as claimed in claim 1, wherein the sensing film is of $SnO_2$ doped with 1 wt % of palladium.

17. The thin film gas sensor as claimed in claim 16, wherein the thickness of the sensing film is 1000 Angstroms to Angstroms.

* * * * *